United States Patent
Park et al.

(10) Patent No.: US 10,085,666 B2
(45) Date of Patent: Oct. 2, 2018

(54) METHOD FOR MEASURING SOCIAL RELATIONSHIP USING HEART RHYTHM COHERENCE (HRC)

(71) Applicants: SANGMYUNG UNIVERSITY SEOUL INDUSTRY-ACADEMY COOPERATION FOUNDATION, Seoul (KR); CENTER OF HUMAN-CENTERED INTERACTION FOR COEXISTENCE, Seoul (KR)

(72) Inventors: Sang In Park, Seoul (KR); Min Cheol Whang, Gyeonggi-do (KR); Myoung Ju Won, Chungcheongnam-do (KR); Sung Teac Hwang, Seoul (KR)

(73) Assignees: SANGMYUNG UNIVERSITY SEOUL INDUSTRY-ACADEMY COOPERATION FOUNDATION (KR); CENTER OF HUMAN-CENTERED INTERACTION FOR COEXISTENCE (KR)

( * ) Notice: Subject to any disclaimer, the term of this patent is extended or adjusted under 35 U.S.C. 154(b) by 0 days.

(21) Appl. No.: 15/306,693

(22) PCT Filed: Jun. 19, 2014

(86) PCT No.: PCT/KR2014/005398
§ 371 (c)(1),
(2) Date: Oct. 25, 2016

(87) PCT Pub. No.: WO2015/194689
PCT Pub. Date: Dec. 23, 2015

(65) Prior Publication Data
US 2017/0042438 A1     Feb. 16, 2017

(30) Foreign Application Priority Data
Jun. 18, 2014  (KR) .................. 10-2014-0074510

(51) Int. Cl.
*A61B 5/0452*    (2006.01)
*G06F 19/00*    (2018.01)
(Continued)

(52) U.S. Cl.
CPC ........ *A61B 5/0452* (2013.01); *A61B 5/02405* (2013.01); *A61B 5/165* (2013.01);
(Continued)

(58) Field of Classification Search
None
See application file for complete search history.

(56) References Cited

U.S. PATENT DOCUMENTS 8,764,673 B2 *  7/2014  McCraty ................ A61B 5/024
                                                600/508

FOREIGN PATENT DOCUMENTS

JP          07021146       1/1995
JP        2006102265       4/2006
(Continued)

OTHER PUBLICATIONS

Bennett, et al. (2002). Huygens's clocks. Proceedings: Mathematics, Physical and Engineering Sciences, 458, 563-579.
(Continued)

*Primary Examiner* — Brian T Gedeon
(74) *Attorney, Agent, or Firm* — Perman & Green, LLP

(57) ABSTRACT

A method for determining a social relationship includes detecting electrocardiogram (ECG) data from at least two subjects, detecting heart rhythm coherence (HRC) data from the ECG signals of the two subjects, and determining a
(Continued)

relationship (intimacy) between the two subjects by comparing the HRC data of the two subjects.

11 Claims, 8 Drawing Sheets

(51) Int. Cl.
  *G16H 50/30*    (2018.01)
  *A61B 5/024*    (2006.01)
  *A61B 5/16*     (2006.01)
  *A61B 5/00*     (2006.01)
  *A61B 5/0245*    (2006.01)

(52) U.S. Cl.
  CPC .............. *G06F 19/00* (2013.01); *G16H 50/30* (2018.01); *A61B 5/0245* (2013.01); *A61B 5/7203* (2013.01)

(56) References Cited

FOREIGN PATENT DOCUMENTS

| | | |
|---|---|---|
| KR | 20010057875 | 7/2001 |
| KR | 20130129714 | 11/2013 |

OTHER PUBLICATIONS

Schmidt, et al. (2008). Coordination: Neural, behavioral and social dynamics. Springer. ISBN 9783540744764, DOI 10.1007/978-3-540-74479-5.

Burgoon, et al. (2007). Interpersonal adaptation: Dyadic interaction patterns. Cambridge University press.

Lakens (2010). Movement synchrony and perceived entitativity. Journal of Experimental Social Psychology, 46(5), 701-708.

Krueger, et al. (2012). Gestural coupling and social cognition: Mobius syndrome as a case study. Frontiers in human neuroscience, 6.

Yun, et al. (2012). Interpersonal body and neural synchronization as a marker of implicit social interaction. SCI REP-UK, 2(959).

Miles, et al. (2010). Too late to coordinate: Contextual influences on behavioral synchrony. European Journal of Social Psychology, 40(1), 52-60.

Pan, et al. (1985). A real-time QRS detection algorithm. IEEE Transactions on Biomedical Engineering, 3, 230-236.

International Search Report, International Application No. PCT/KR2014/005398, dated Mar. 16, 2015.

* cited by examiner

Heart Rhythm Coherence

METHOD FOR MEASURING SOCIAL RELATIONSHIP USING HEART RHYTHM COHERENCE (HRC)

CROSS-REFERENCE TO RELATED APPLICATIONS

This application is the National Stage of International Application No. PCT/KR2014/005398, having an International Filing Date of 19 Jun. 2014, which designated the United States of America, and which International Application was published under PCT Article 21 (2) as WO Publication No. 2015/194689 A1, and which claims priority from and the benefit of Korean Application No. 10-2014-0074510, filed on 18 Jun. 2014, the disclosures of which are incorporated herein by reference in their entirety.

BACKGROUND

1. Field

The presently disclosed embodiment relates to methods of measuring a social relationship, and more particularly, to an intimacy measuring method based on heart rhythm coherence (HRC) and a system using the intimacy measuring method.

2. Brief Description of Related Developments

Social cognition or social interaction denotes understanding of a mental state or behavior of a target of communication. A sympathetic reaction with other people is required to understand mental states or behaviors of the other people (Krueger, et al. "Gestural Coupling and Social Cognition: Mobius Syndrome as a Case Study". Frontiers in Human Neuroscience, Vol. 6, 2012). Many researches into social cognition or social interaction have been recently being conducted. In these researches, synchronization or entrainment is considered as an important concept. Synchronization is a phenomenon in which, when people socially interact with one another, biorhythms of the people are harmonized (Yun, et al. "Interpersonal Body and Neural Synchronization as a Marker of Implicit Social Interaction". Scientific Reports, Issue 2:959, December, 2012). This synchronization phenomenon may not only occur between people but also in objects or natural phenomena. For example, when pendulums of several clocks swing horizontally at different speeds, the pendulums may swing horizontally in the same direction and at the same speed due to synchronization (Bennett, et al. "Huygens's Clocks". The Royal Society, Issue 458, pp. 563-579 2002), and firefly lights that are twinkling individually are synchronized at one moment and then simultaneously twinkle together at the same speed (Buck, et al. "Synchronous Fireflies". Scientific American, Issue 234, pp. 74-85, 1976).

This synchronization phenomenon occurs among people. A representative example of the synchronization is a phenomenon in which two people walk in step with each other at the same interval (Schmidt, et al. "Coordination: Neural, Behavioral, and Social Dynamics". Springer, 2008; Burgoon, et al. "Interpersonal Adaptation: Dyadic Interaction Patterns". Cambridge University Press, 1995). In a study of Yun, et al., (2012), synchronizations between finger movements occurred unconsciously between two subjects were compared. This study reported that synchronization between finger movements of two subjects occurred and neural activation of the brain greatly increased when the two subjects perform a cooperative operation, compared with when the two subjects do not perform a cooperative operation. In another study, synchronizations between finger movements of subjects were compared, and it was reported that greater synchronization occurred when the fingers of the subjects move at the same speed than when the fingers of the subjects move at different speeds (Lakens, Daniël. "Movement Synchrony and Perceived Entitativity". Journal of Experimental Social Psychology, Volume 46, Issue 5, pp. 701-708, September, 2010). It was reported that this synchronization of body movements relates to an increase in a positive relationship between people (Miles et al. "Too Late to Coordinate: Contextual Influences on Behavioral Synchrony". European Journal of Social Psychology, Issue 40, pp. 52-60, September 2009).

As mentioned above, synchronization of unconscious behaviors causes not only synchronization of bodies but also synchronization of biological reactions and a positive effect. However, a sympathetic reaction is very important in interactions between people, and may differently appear according to with whom a person maintains a social relationship and communicates. This social relationship is socially strong or weak. However, current studies into social relationships are not considered in synchronization. Accordingly, it is expected that there is a difference in the degree of synchronization between physiological reactions according to social relationships. This is because physiological reactions generated according to social relationships are unconscious. It has been recently reported that synchronization of physiological reactions effectively affects maintenance and increase of a social relationship.

SUMMARY

The presently disclosed embodiment provides a method of quantitatively estimating a social relationship via synchronization between heart rhythms.

The presently disclosed embodiment provides a method of estimating a social relationship or intimacy between two persons via an interindividual heart entrainment analysis, and a system that uses the method.

According to an aspect of the presently disclosed embodiment, there is provided a method of determining a social relationship, the method including detecting electrocardiogram (ECG) data from at least two subjects; detecting heart rhythm coherence (HRC) data from ECG signals of the two subjects; and determining a relationship (intimacy) between the two subjects by comparing the HRC data of the two subjects.

According to an aspect of the presently disclosed embodiment, the HRC data may be extracted from heart rhythm variability (HRV) obtained via a Fast Fourier Transform (FFT).

According to another aspect of the presently disclosed embodiment, the HRV data may be acquired from R-peak to R-peak Interval (RRI) data extracted from the ECG data.

According to another aspect of the presently disclosed embodiment, the HRV data may be obtained by extracting the RRI data from the ECG data; converting the RRI data into time series data; and FFT-analyzing the time series data.

According to another aspect of the presently disclosed embodiment, the HRC data may include a dominant peak frequency and a dominant peak amplitude extracted in an HRC band of the HRV.

According to another aspect of the presently disclosed embodiment, a difference between dominant peak frequencies of HRC signals of the two subjects, a difference between dominant peak amplitudes of the HRC signals of the two subjects, and an r square obtained via a correlation analysis of each of the HRC signals may be used as variables for determining the degree of synchronization between the two subjects.

According to another aspect of the presently disclosed embodiment, there is provided a social relationship determining system for performing the above-described method, the system including a sensor configured to extract ECG data from the subjects; a display configured to present a specific facial expression to at least one of the subjects; a data processor configured to process the ECG data of the subjects obtained by the sensor; and an analyzer configured to analyze intimacy between subjects by analyzing the data.

The presently disclosed embodiment may estimate a social relationship between two people via an inter-individual heart entrainment analysis. The inter-individual heart entrainment analysis uses the synchronization degree of heart rhythms between two people. In an intimacy estimating method according to the presently disclosed embodiment, a social relationship between two people may be quantitatively estimated, and it is expected that the estimated social relationship helps to ease asocial pathological phenomenon.

DETAILED DESCRIPTION

A method and system for measuring an interpersonal relationship or intimacy according to an aspect of the presently disclosed embodiment will now be described more fully with reference to the accompanying drawings.

In modern society, people need to contact and communicate with many other people. The media has often and recently released the story of people who fail to adapt to this society environment and thus fall behind. Although not so much serious as in the above case, anyone has a fear or worry of social relationships. In order to recover social relationships, the social relationships need to be quantitatively estimated first, and then solutions thereof may be suggested.

Via a description of the aspect below, the presently disclosed embodiment provides a method of quantitatively estimating a social relationship between people, and may improve social relationships and address a pathological phenomenon via this method.

1. Subjects 72 university students (36 men and 36 women having average ages of 24.27±2.24) participated in an experiment. The subjects participated in this experiment were people having relationships over three or more years and making pairs, and the collected people have the same sex in order to prevent a sexual effect. Neither of the subjects had disorder nor disease in cardiovascular and nervous systems and took sufficient sleeps the day before. Further, the subjects were prohibited from taking in caffeine, cigarette, and alcohol that may affect a cardiovascular reaction. Before the experiment, all of the subjects received a general explanation of the experiment except for the purpose of the experiment and then underwent the experiment and got paid a certain amount of money in return for the experiment.

2. Experiment Method

The subjects participated in the experiment were divided into a strong social relationship group (friend) and a weak social relationship group (stranger) based on a relationship period. The strong social relationship group includes friends having relationships over three or more years and making pairs, and the weak social relationship group includes strangers making pairs. To determine social relationships of collected subjects, a simple survey asking a birthday, family members, hobbies, and the like was conducted, and only subjects having passed the survey were participated in the experiment.

Figure 1:
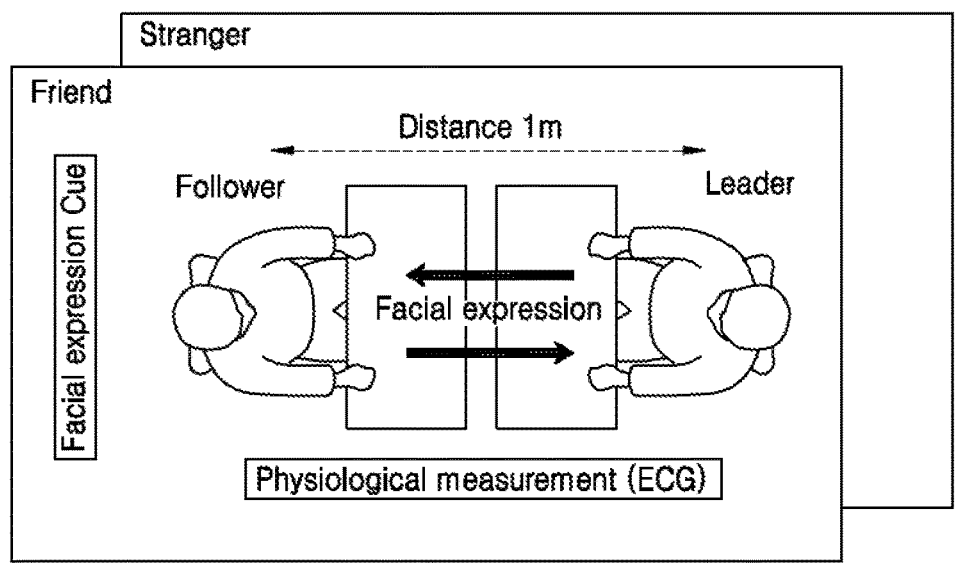
FIG. 1 illustrates an example of a method of checking an electrocardiogram (ECG) from measurement data of two subjects in order to detect heart rhythm coherence (HRC) from the two subjects according to the presently disclosed embodiment.
Figure 2:
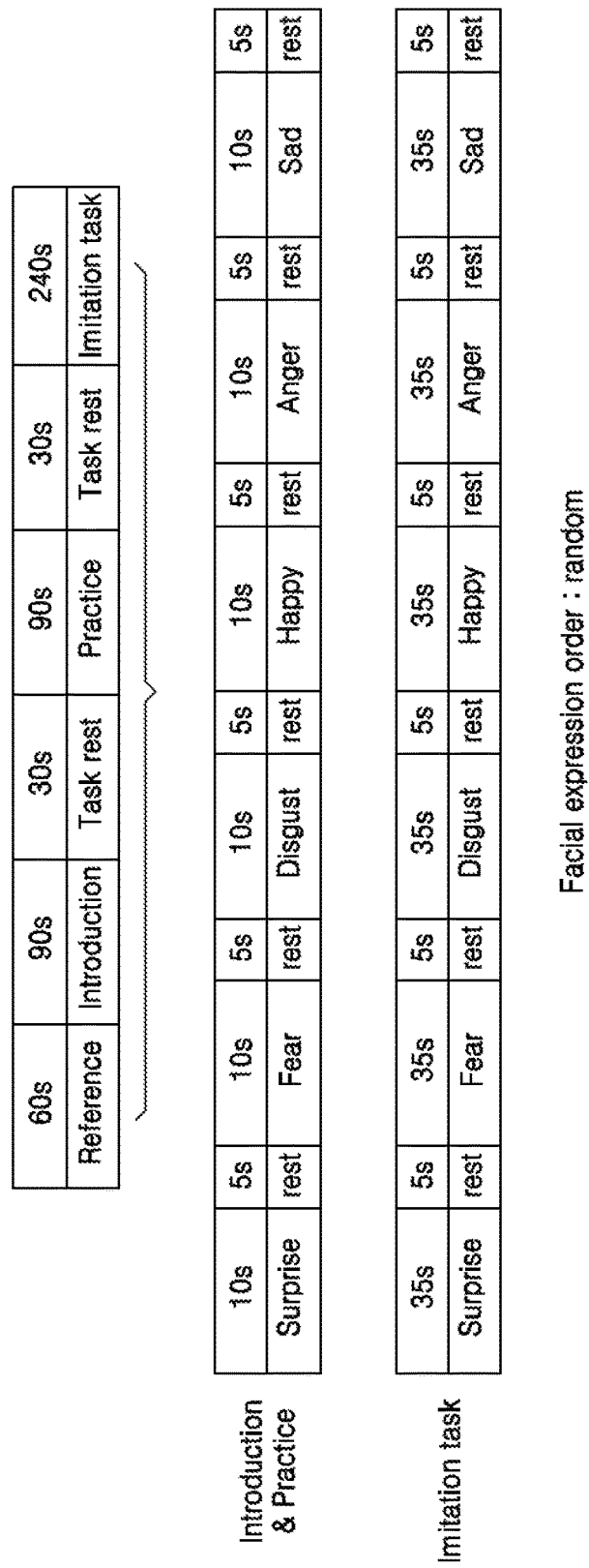
FIG. 2 explains a sequence of facial expression presentation and imitation between subjects when HRC is detected.

The subjected divided into two groups were also divided into leaders and followers. As shown in FIG. 1, a leader and a follower, who are two subjects, sit on comfortable chairs while facing each other. A distance between the two subjects was fixed to 1 m. The two subjects were instructed to interact with each other through facial expressions regarding 6 basic emotions defined by Ekman, namely, fear, disgust, fear, surprise, anger, and happiness. At this time, the leader was instructed to make a face according to a facial expression guideline suggested via a screen, and the follower was instructed to follow the facial expression of the leader. During the experiment, electrocardiogram (ECG) was measured to compare the heart rhythms of the two people with each other. As shown in FIG. 2, a total of experiment tasks include a reference task of 60 seconds, an introduction task of 90 seconds, a practice task of 90 seconds, and an imitation task of 240 seconds. A task rest of 30 seconds was included between adjacent tasks, and the introduction task and the practice task were included in the experiment so that the subjects may make natural faces in the imitation task. The above-described experiment process was conducted on two groups, subjects were crossed between the two groups and then the above-described experiment process was conducted again thereon, and the roles of the leader and the follower were fixed.

For example, if there are friend groups A (leader a, follower b) and friend groups B (leader c, follower d) as subject groups, tasks are performed between groups A, and tasks are performed between the groups B. This is a task when people are intimate. A leader a in a subject group A and a follower d in a subject group B perform tasks, and a leader c in the group B and a follower b in the group A perform tasks. This is a task when people are not intimate. In this way, a total of 36 groups of subjects were participated in the experiment, two random groups were bound together and cross-performed the tasks, and the roles of a leader and a follower do not change. In other words, a leader in a task with respect to an intimate group played a role of a leader in a task with respect to a stranger group.

Each in the overall tasks in FIG. 2 is performed as follows.

Reference Task:

Biometric data of a base line is acquired when no stimulus is presented, before a stimulus is presented.

Introduction Task:

The type and shape of a facial expression are learned to make a smooth face in a main task (imitation task).

Task Rest:

A subject takes a rest between tasks in order to minimize a (remaining) effect of a stimulus presented in a previous task and to reduce an effect on a stimulus in a next task.

Practice Task:

A facial expression is imitated and practiced to make a smooth face in the main task.

Task Rest:

A subject takes a rest between tasks in order to minimize a stimulus effect of a task presented previously and to reduce an effect on a stimulus in a next task.

Imitation Task:

A leader makes a presented face, and a follower imitates the face made by the leader. At this time, ECG detection is performed in real time.

In all of the introduction, practice, and imitation tasks, facial expressions of 6 basic emotions (i.e., fear, disgust, fear, surprise, anger, and happiness) are presented. In the introduction and practice tasks, each facial expression is presented for 10 seconds. In the imitation task, each facial expression is presented for 35 seconds. 5 seconds of rest is included between facial expressions. The order in which the 6 facial expressions are presented is randomly determined, and a facial expression is not selected but the 6 facial expressions are imitated and practiced.

3. Analysis Method

Figure 9:
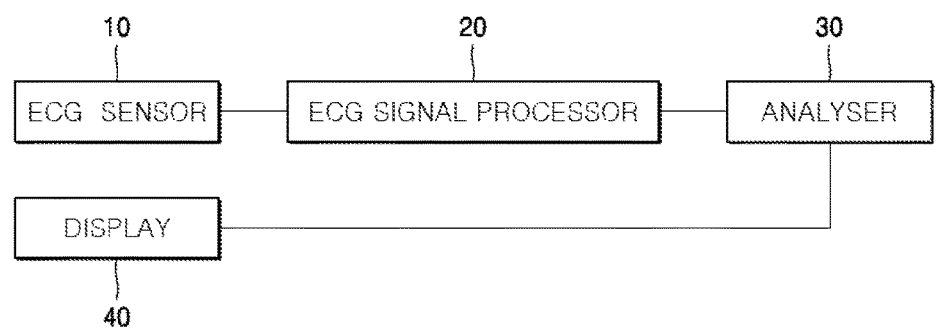
FIG. 9 is a schematic block diagram of an analysis system according to the presently disclosed embodiment.

An analysis method according to the present invention uses an analysis system having a structure as illustrated in FIG. 9. The analysis system according to the present invention includes an ECG sensor 10 for detecting an ECG signal (data) from subjects, a signal processor 20 for pre-processing the ECG signal, an analyzer 30 for estimating intimacy between the subjects by detecting heart rhythm coherence (HRC) data from a pre-processed ECG signal, and a display for presenting a facial expression to one of the subjects. The display may have a structure of a single display or a multi-display including a display for presenting a facial expression and a display for display a result of the facial expression. The analysis system according to the present invention including these elements is entirely based on a computer, and thus a peripheral device such as a keyboard, a mouse, or a printer may be selectively added.

The ECG signal (data) was sampled with 500 Hz via a lead-I method. In the experiment according to the presently disclosed embodiment, the ECG signal was acquired by amplifying a signal via an MP100 power supply and an ECG 100C amplifier (Biopac systems Inc., USA) and converting an analog signal into a digital signal via NI-DAQ-Pad9205 (National instruments, USA). The acquired ECG signal detected an R-peak via a QRS detection algorithm (Pan et al. "A Real-Time QRS Detection Algorithm". IEEE Transactions on Biomedical Engineering, Volume BME-32, No. 3, pp. 230-236, March, 1985). The detected R-peak extracted a R-peak to R-peak interval (RRI) by excluding noise and using a difference between normal R-peak intervals.

Figure 3:
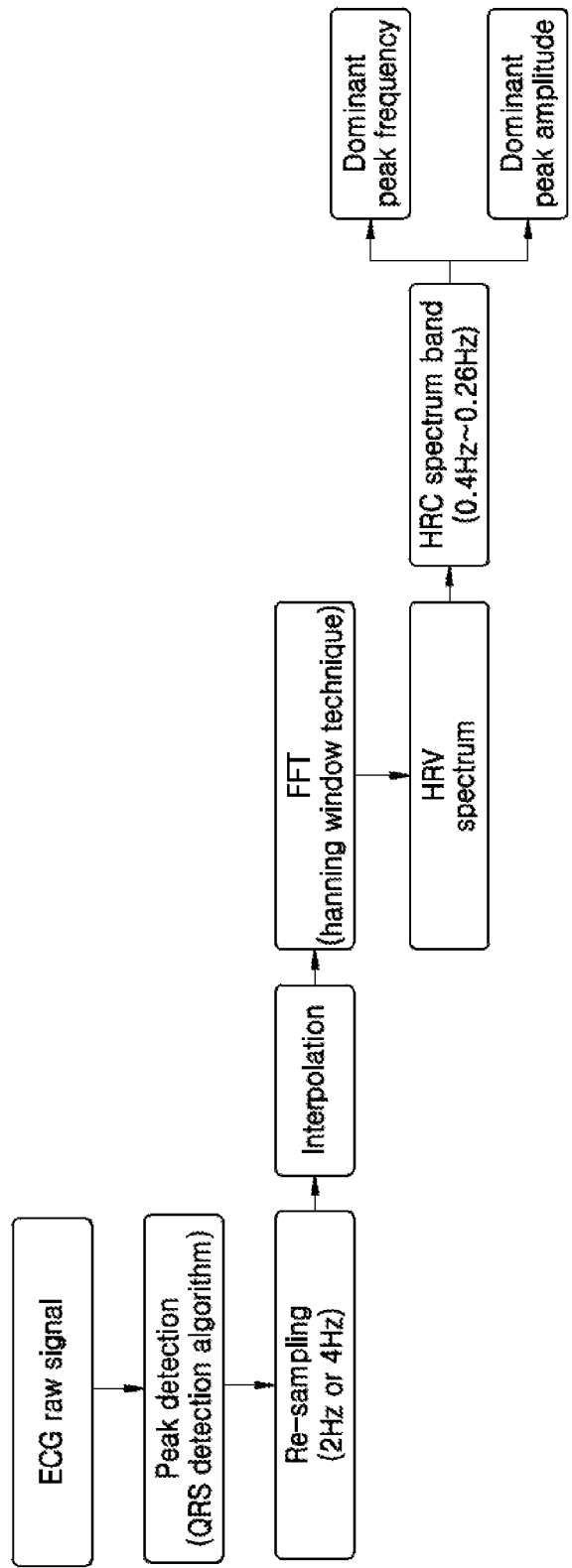
FIG. 3 is a flowchart of ECG signal processing for HRC detection.

FIG. 3 is a block diagram illustrating a signal processing sequence. Referring to FIG. 3, RRI data undergoes interpolation after being resampled with 2 Hz in order to be converted to time series data. Then, an Heart Rate Variability (HRV) spectrum is extracted via a Fast Fourier Transform (TFT) analysis with respect to the interpolated data. Data in an HRC band (0.4 Hz to 0.26 Hz) is extracted from the extracted HRV spectrum data, and a dominant peak frequency and a dominant peak amplitude are extracted from the extracted data in the HRC band.

According to the presently disclosed embodiment, synchronization of the heart is analyzed via HRC between two people, and a social relationship is estimated by using the analyzed synchronization.

HRC variables for use in a heart synchronization analysis are the extracted dominant peak frequency and the extracted dominant peak amplitude. A difference between variables of two people is calculated, and it is determined that, the smaller the difference is, the higher synchronization between two signals is. An r square value is extracted via a correlation analysis of an HRC signal and utilized as a variable for determining the degree of synchronization.

Figure 4:
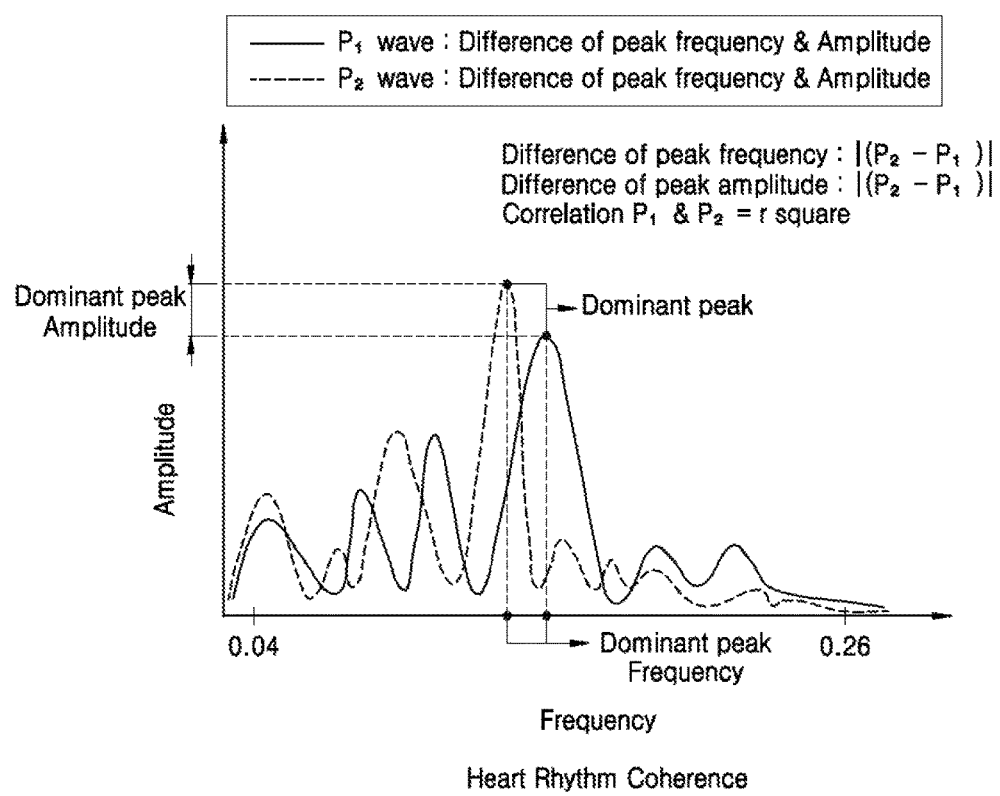
FIG. 4 is a graph for explaining HRC variables.

FIG. 4 is a graph for explaining variables used in intimacy recognition.

The graph of FIG. 4 shows signals in an HRC spectrum band (0.04 Hz to 0.26 Hz) in order to extract peak power and frequency from an HRV spectrum (0 Hz to 0.4 Hz) via an FFT analysis of an ECG signal. In the graph of FIG. 4, P1 and P2 indicate a leader and a follower as subjects who perform tasks, respectively. Differences between dominant peak amplitude values of two subjects and between dominant peak frequency values of the two subjects were used as variables, and an r square ($r^2$) value was used as a variable by squaring an r (correlation coefficient) value obtained by correlation-analyzing signals of the two subjects.

$$r^2 = \left( \frac{\sum_{i=1}^{n} (x_i - \bar{x})(y_i - \bar{y})}{\sqrt{\sum_{i=1}^{n} (x_i - \bar{x})^2} \cdot \sqrt{\sum_{i=1}^{n} (y_i - \bar{y})^2}} \right)^2 \quad \text{[Equation 1]}$$

$x = HRC$ spectrum band (0.04-0.26 Hz) signals of leader $y = HRC$ spectrum band (0.04-0.26 Hz) signals of follower $\bar{x} =$ Average of $HRC$ spectrum band (0.04-0.26 Hz) signals of leader $\bar{y} =$ Average of $HRC$ spectrum band (0.04-0.26 Hz) signals of follower Data of 32 people among 72 subjects participated in the present experiment was used to generate a rule base, and the remaining 40 subjects were utilized to verify the rule base. The rule base will be described later.

4. Analysis Result

Figure 5:
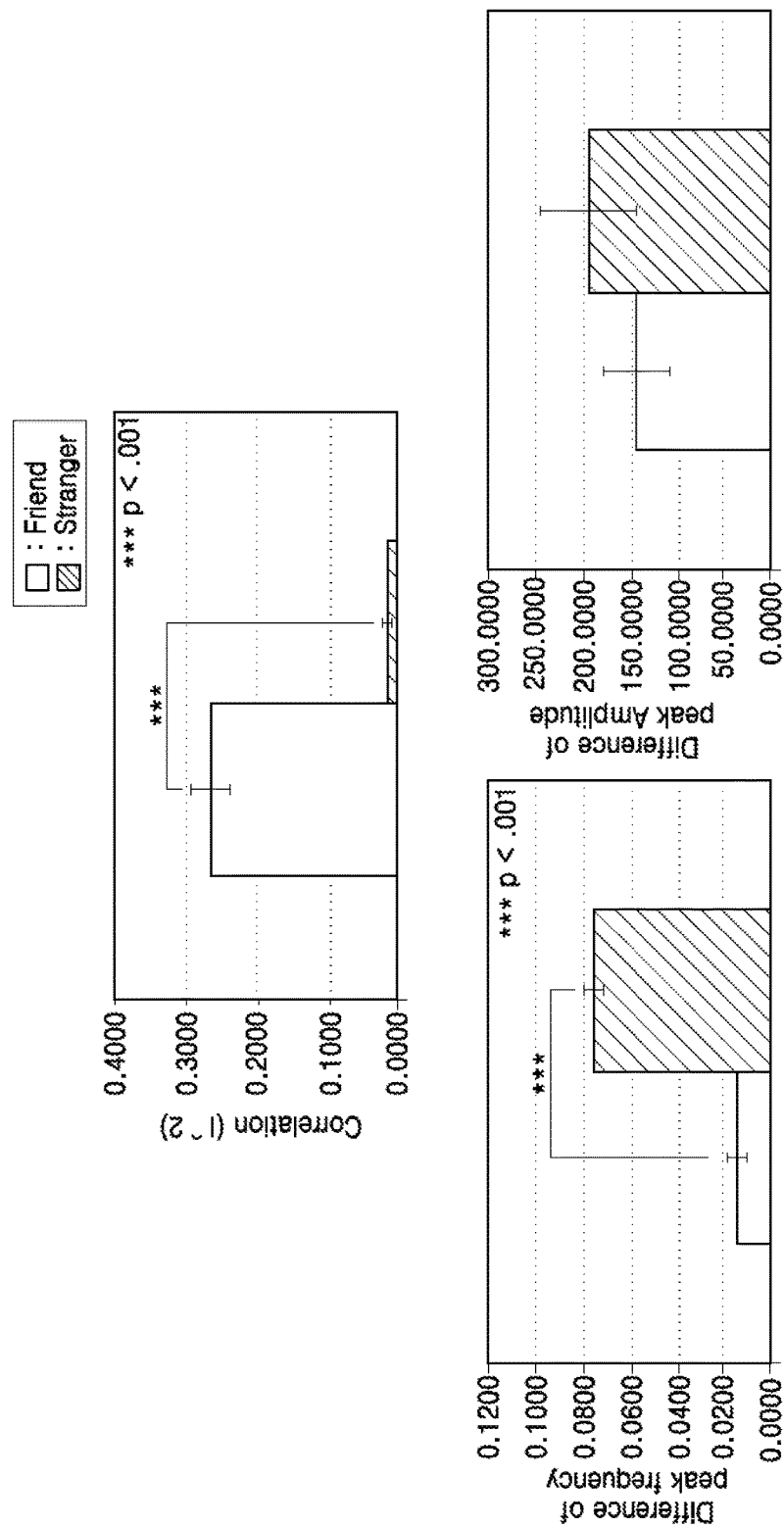
FIG. 5 is a Frequency-Power Spectrum Density (PSD) graph showing a result of an HRC analysis of a leader and a follower in each of a friend group and a stranger group.

FIG. 5 is a Frequency-Power Spectrum Density (PSD) graph showing an example of HRC of a leader and a follower in each of a friend group and a stranger group. As can be seen from an HRC pattern of each group, the friend group has a higher entrainment of HRC data of a leader and a follower and a smaller difference in peak frequency than the stranger group.

Figure 6:
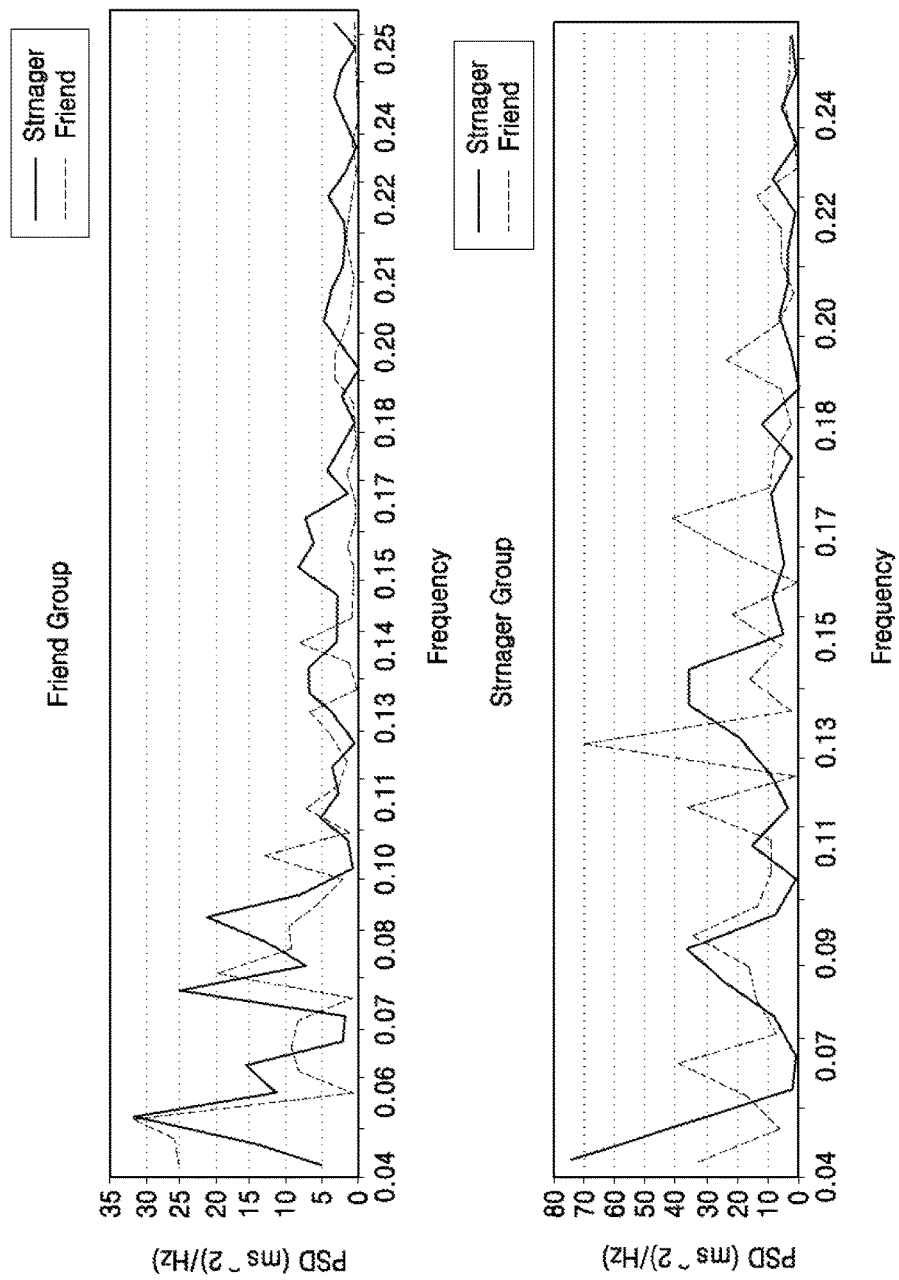
FIG. 6 shows a statistical analysis result of HRC of a leader and a follower in each of a friend group and a stranger group.

FIG. 6 shows a statistical analysis result of HRC of a leader and a follower in each of a friend group and a stranger group. It was checked from FIG. 6 that an r square (correlation) according to a correlation analysis of the friend group statistically significantly increased compared with that of the stranger group. In other words, a statistical significance level p represents a high reliability that is smaller than 0.001 (p<0.001), namely, a high reliability of 99.9% or greater.

It was also checked from FIG. 6 that a difference of peak frequency of the friend group statistically significantly decreased compared with that of the stranger group (p<0.001). However, it was not confirmed that there was a statistically significant difference between peak amplitudes of the friend group and the stranger group (p>0.05).

Figure 7:
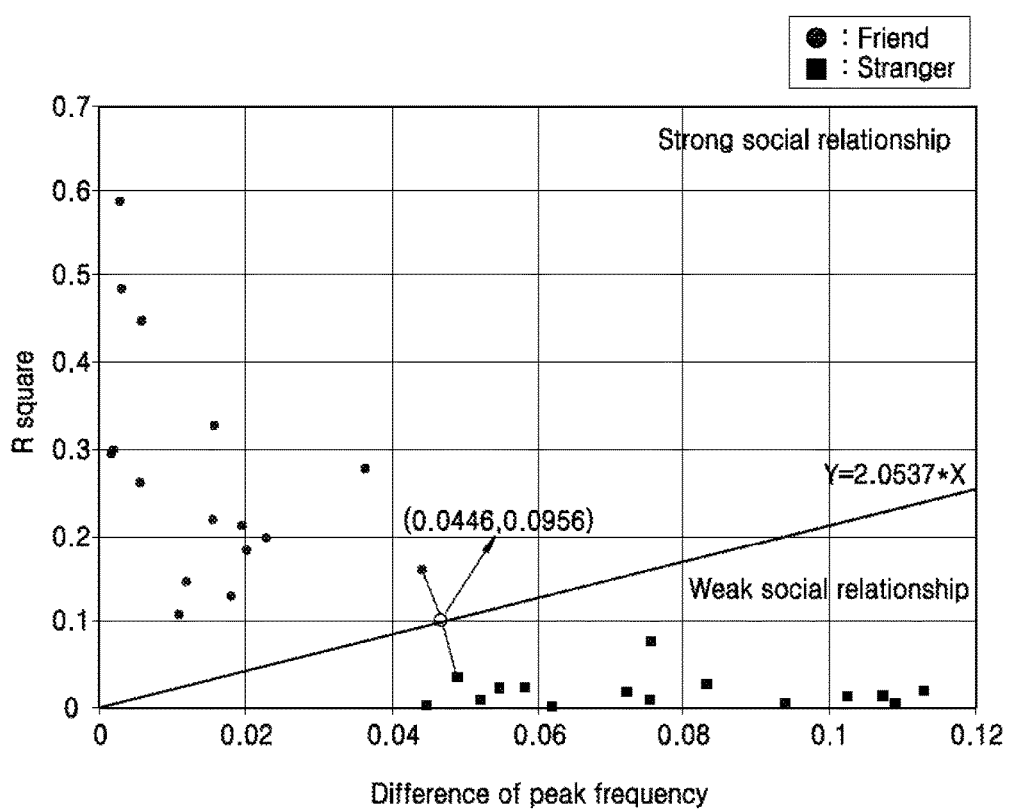
FIG. 7 is a graph for explaining a rule base for determining a social relationship (intimacy) due to HRC variables.

A rule base capable of distinguishing social relationships via a variable representing a statistically significant difference between two groups was made as shown in FIG. 7. Two variables used in a rule base are an r square and a difference of peak frequency and are defined as an X axis and a Y axis, and thus data of subjects participated in the experiment was plotted on an X-Y coordinate. An equation of a straight line passing through a center of two data that are the closest to each other among the data of two groups, for example, (0.044, 0.095) and (0, 0), was deduced as a rule base. Data above the deduced straight line equation was defined as a strong social relationship, and data below the deduced straight line equation was defined as a weak social relationship. The deduced straight line equation is as follows:

$$Y=2.0537*X \quad \text{[Equation 2]}$$

The above linear equation is a rule base that determines intimacy by using a critical function (general formula) determined via experimental data of 32 people.

Figure 8:
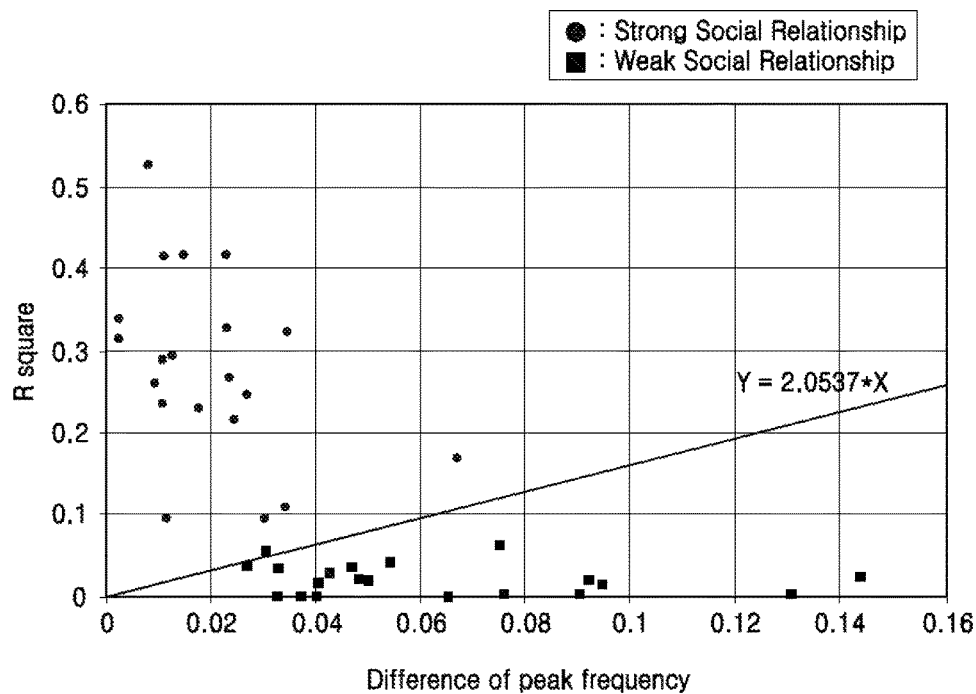
FIG. 8 is a graph showing a result of a rule base verification using HRC obtained from a new group for verification.

A result of a verification of a rule base of HRC is as sown in FIG. 8. As described above, an HRC variable was extracted from the remaining 40 subjects who are not experimented and was used in the verification of the rule base.

According to a result of a verification of a rule base of HRC, all of the data of the total of 20 groups were classified into a strong social relationship (accuracy of a strong social relationship: (20/20)*100%=100%). The data of 19 groups among the data of the total of 20 groups were classified into a weak social relationship, and only the data of one group was classified into a strong social relationship (accuracy of a weak social relationship: (19/20)*100%=95%). The data accuracy of the overall 40 groups was verified to be 95% (accuracy: (39/40)*100%=97.5%).

As described above, the presently disclosed embodiment estimates a social relationship between two people via an inter-individual heart entrainment analysis. In the inter-individual heart entrainment analysis, the synchronization degree of heart rhythm between two people was used, and intimacy estimation may be very accurately performed. According to the presently disclosed embodiment, a social relationship between two people may be quantitatively estimated and may be used to ease or address a social pathological phenomenon.

While the inventive concept has been particularly shown and described with reference to exemplary aspects thereof, it will be understood that various changes in form and details may be made therein without departing from the spirit and scope of the following claims.

What is claimed is:

1. A method of determining a social relationship, the method comprising:
   detecting, with an electrocardiogram (ECG) sensor, ECG data from at least two subjects for processing, with a data processor, ECG signals of the at least two subjects from the ECG sensor, that embodies the ECG data;
   defining, with the data processor, a heart rhythm coherence (HRC) data spectrum of the at least two subjects from the processed ECG signals of the two subjects;
   extracting, with the data processor, a difference X value between dominant peak frequencies of the HRC data spectrum of the two subjects;
   extracting, with the data processor, an r square value via a correlation analysis of each of the HRC data spectrum;
   determining, with an intimacy analyzer coupled to the data processor, a social relationship between the two subjects by using the following equation: $Y=2.0537*X$, where Y is a result value, wherein the social relationship is determined as being strong when the r square value is larger than the result value Y, otherwise, the social relationship is determined as being weak; and
   displaying, with a display coupled to the data processor, a strength of the social relationship based on a comparison of the result value Y with the r square value.

2. The method of claim 1, wherein the HRC data spectrum is extracted, by the data processor, from heart rhythm variability (HRV) data obtained via a Fast Fourier Transform (FFT).

3. The method of claim 2, wherein the HRV data is acquired from R-peak to R-peak Interval (RRI) data extracted from the ECG data.

4. The method of claim 3, wherein the HRV data is obtained by:
   extracting the RRI data from the ECG data;
   converting the RRI data into time series data; and
   FFT-analyzing the time series data.

5. The method of claim 2, wherein the HRC data spectrum comprises a dominant peak frequency and a dominant peak amplitude extracted in an HRC band of the HRV data.

6. A social relationship determining system for performing the method of claim 1, the system comprising:
   the ECG sensor, the ECG sensor being configured to extract ECG data from the subjects;
   the display configured to present a specific facial expression to at least one of the subjects;
   the data processor configured to process the ECG data of the subjects obtained by the sensor; and
   the intimacy analyzer configured to analyze intimacy between subjects by analyzing the ECG data.

7. The social relationship determining system of claim 6, wherein the HRC data spectrum is extracted, by the data processor, from heart rhythm variability (HRV) data obtained via a Fast Fourier Transform (FFT).

8. The social relationship determining system of claim 7, wherein the HRV data is acquired from R-peak to R-peak Interval (RRI) data extracted from the ECG data.

9. The social relationship determining system of claim 8, wherein the data processor extracts RRI data from the ECG data, and generates the HRV data spectrum by converting the RRI data into time series data.

10. The social relationship determining system of claim 7, wherein the HRC data spectrum comprises a dominant peak frequency extracted in an HRC band of the HRV data.

11. The social relationship determining system of claim 10, wherein the intimacy analyzer determines the degree of synchronization between the two subjects by using the difference between dominant peak frequencies of HRC signals of the two subjects and the r square value.

* * * * *

UNITED STATES PATENT AND TRADEMARK OFFICE
CERTIFICATE OF CORRECTION

PATENT NO.        : 10,085,666 B2
APPLICATION NO.   : 15/306693
DATED             : October 2, 2018
INVENTOR(S)       : Park et al.

It is certified that error appears in the above-identified patent and that said Letters Patent is hereby corrected as shown below:

On the Title Page

Under Applicants, item (71), first listed Applicant, "ACADENY" should read --ACADEMY--.

Under ABSTRACT, item (57), first line of the ABSTRACT "for" should read --of--.

Signed and Sealed this
Sixteenth Day of April, 2019

Andrei Iancu
*Director of the United States Patent and Trademark Office*